United States Patent [19]

Fukumoto et al.

[11] Patent Number: 4,569,224
[45] Date of Patent: Feb. 11, 1986

[54] DEVICE FOR MEASURING THE ABSOLUTE VALUE OF THE DENSITY OF SALTS IN ATMOSPHERE

[75] Inventors: Takaaki Fukumoto, Kishiwada; Yasukazu Mukogawa, Osaka; Masaharu Hama; Motonori Yanagi, both of Itami, all of Japan

[73] Assignee: Mitsubishi Denki Kabushiki Kaisha, Tokyo, Japan

[21] Appl. No.: 667,721

[22] Filed: Nov. 2, 1984

[30] Foreign Application Priority Data

Dec. 15, 1983 [JP] Japan .................................. 58-238602

[51] Int. Cl.⁴ .............................................. G01N 27/26
[52] U.S. Cl. .................................... 73/32 R; 204/400; 204/409; 324/439
[58] Field of Search ................. 73/23, 19, 32 R, 28; 204/1 A, 409; 324/439, 450, 65 R; 422/88, 90

[56] References Cited

U.S. PATENT DOCUMENTS

| | | | |
|---|---|---|---|
| 2,758,079 | 8/1956 | Eckfeldt | 324/439 |
| 3,267,361 | 8/1966 | Maddox | 324/439 |
| 3,493,857 | 2/1970 | Silverman | 324/65 R |
| 3,751,967 | 8/1973 | Fick et al. | 73/23 |
| 4,083,766 | 4/1978 | Landon et al. | 324/439 |

Primary Examiner—Stephen A. Kreitman
Attorney, Agent, or Firm—Birch, Stewart, Kolasch & Birch

[57] ABSTRACT

A device for measuring the absolute value of the density of salts in atmosphere, which comprises: an airtight water tank containing super pure water of a predetermined quantity; a means for bubbling a predetermined quantity of air in atmosphere for a predetermined time into the super pure water to make the salts in the air dissolve in the water; a means for exhausting the super pure water after the bubbling; and a sodium ion analyzer for measuring the density of sodium ions in the exhausted super pure water of a predetermined quantity.

1 Claim, 2 Drawing Figures

DEVICE FOR MEASURING THE ABSOLUTE VALUE OF THE DENSITY OF SALTS IN ATMOSPHERE

FIELD OF THE INVENTION

The present invention relates to a device for measuring the absolute value of the density of salts in the atmosphere and continuously monitoring the same.

BACKGROUND OF THE INVENTION

In order to explain the background of the invention, reference will be particularly made to FIG. 1 showing a prior art device for measuring the density of salts in atmosphere. In the FIGURE, the reference numeral 1 designates a water tank which contains super pure water the resistivity of which is above 15MΩcm. The top of the tank 1 is opened to the atmosphere. The reference numeral 3 designates a pipe for supplying the super pure water continuously to the tank 1 at a constant flow rate. The reference numeral 2 designates a valve provided at the pipe 3. The reference numeral 4 designates an exhaust pipe for exhausting the super pure water in the tank 1. The numerals 5 and 6 designate a sodium ion analyzer and a resistivity meter provided at the exhaust outlet of the exhaust pipe 4 for measuring the density of Na+ ions in the exhausted super pure water.

The device will be operated as follows:

The surface of the water in the tank 1 is in contact with the atmosphere, and the material including Na+ ions, that is, salts in the atmosphere are dissolved naturally into the super pure water. On the other hand, the super pure water in the tank 1 is exhausted to the exhaust outlet through the exhaust pipe 4 continuously at a constant flow rate. The sodium ion analyzer 5 and the resistivity meter 6 measures the density of Na+ ions in the super pure water, which density indicates the relative value of the density of salts in the atmosphere. The analyzer 5 and the meter 6 operate continuously, thereby enabling to monitor the relative value of the density continuously.

Under the prior art device of such construction, it is possible to measure the relative change of the density of salts in the atmosphere continuously. But it is impossible to measure the absolute value of the same.

OBJECTS AND SUMMARY OF THE INVENTION

The present invention is directed to solve the problems pointed out above, and has for its object to provide a device for measuring the absolute value of the density of salts in the atmosphere and continuously monitoring the same.

Other objects and advantages of the present invention will become apparent from the detailed description given hereinafter; it should be understood, however, that the detailed description and specific embodiment are given by way of illustration only, since various changes and modifications within the spirit and scope of the invention will become apparent to those skilled in the art from this detailed description.

According to the present invention, there is provided a device for measuring the absolute value of the density of salts in the atmosphere, which comprises an airtight water tank containing super pure water of a predetermined quantity a means for bubbling a predetermined quantity of air from the atmosphere for a predetermined time into the super pure water to make the salts in the air dissolved into the water; a means for exhausting the super pure water after the bubbling and a sodium ion analyzer for measuring the density of sodium ions in the exhausted super pure water of a predetermined quantity.

DETAILED DESCRIPTION OF THE PREFERRED EMBODIMENTS

Figure 1:
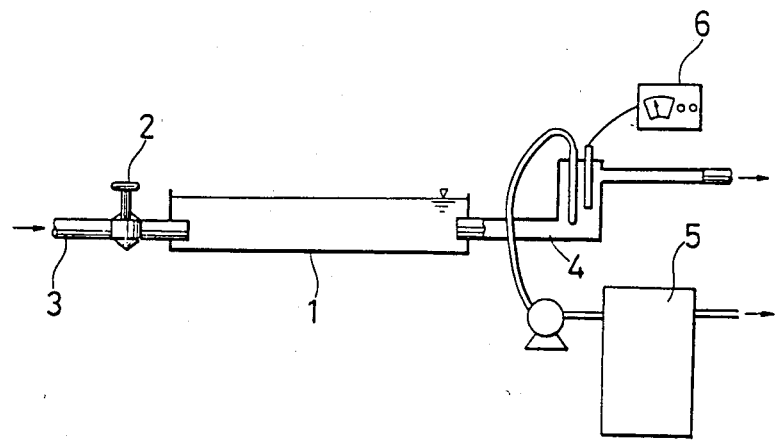
FIG. 1 is a schematic diagram showing a prior art device for measuring the density of salts in the atmosphere.
Figure 2:
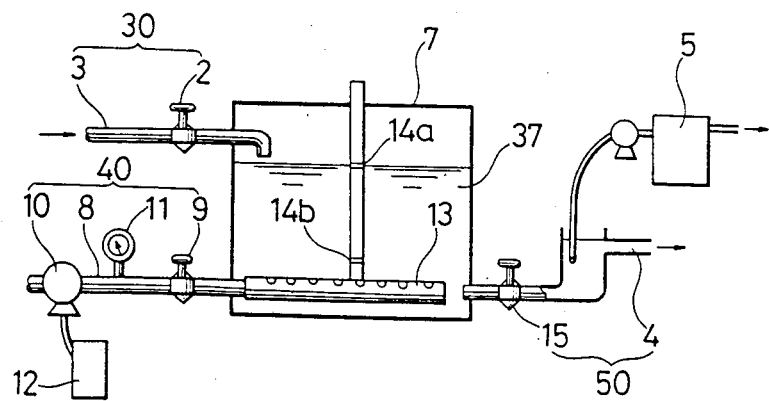
FIG. 2 is a schematic diagram showing a device for measuring the absolute value of the density of salts in the atmosphere as one embodiment of the present invention.

Reference will now be particularly made to FIG. 2 which shows an embodiment of the present invention. In the Figure, the reference numeral 7 designates an airtight water tank of a predetermined capacity which contains the super pure water 37 of a predetermined quantity the resistivity of which is above 15MΩcm. The tank 7 is made of a material from which any dissolved material, including sodium ions, will not soak out, such as a transparent vinyl chloride. The numeral 3 designates a pipe for supplying the super pure water to the tank 7. The numeral 2 designates a valve provided at the pipe 3. The pipe 3 and the valve 2 constitute a means 30 for supplying the water. The numeral 13 designates a bubbling pipe for bubbling the air in the atmosphere into the super pure water 37 in the tank 7 to make the salts in the atmosphere dissolve in the super pure water 37. The numerals 8, 9, 10, 11, and 12 designate a pipe, a valve, a pump, a flow meter, and a timer, all of which constitute a means 40 for supplying the air in the atmosphere to the bubbling pipe 13. The numerals 14a and 14b designate flow switches to hold the level of the super pure water 37 contained in the tank 7 at a constant level. The numeral 4 designates an exhaust pipe for exhausting the super pure water 37 contained in the tank 7 to the outside. The numeral 15 designates a valve provided at the exhaust pipe 4. The exhaust pipe 4 and the valve 15 constitute a means 50 for exhausting the water. The numeral 5 designates a sodium ion analyzer for measuring the density of Na+ ions in the exhausted super pure water of a predetermined quantity. The material taking inlet 5a of the analyzer 5 is sunk in the exhausted water.

The device will be operated as follows:

At first, the valve 2 in the means 30 for supplying the water is opened, and the super pure water 37 the resistivity of which is about 15MΩcm is supplied to the airtight water tank 1 through the pipe 3. When the flow switch 14a operates, the valve 2 in the means 30 for supplying the water is closed to stop the supply of the super pure water 37 to the tank 1. Thus, the airtight water tank 1 is filled up with the super pure water 37 of a predetermined quantity. When the valve 9 in the means 40 for supplying the air in atmosphere is opened and the pump 8 is operated, the air in atmosphere is sent to the bubbling pipe 13 through the pipe 8 at a constant flow rate for a predetermined time. The bubbling pipe 13 operates to bubble the air into the super pure water 37 in the tank 7 to make the salts, that is, NaCl in the air dissolve in the super pure water 37. When the bubbling is concluded, the valve 9 is closed, the valve 15 in the means 50 for exhausting the water is opened, and the super pure water in the tank 7 is exhausted to the outside through the pipe 4 at a constant flow rate caused by its positional potential. The sodium ion analyzer 5 with its material taking inlet 5a sunk in the exhausted super pure water operates to measure the density of Na+ ions in the super pure water. Then, the absolute value of the density of salts in the atmosphere is obtained from the density of Na+ in the super pure water measured by the sodium ion analyzer 5 by executing an operation including the mass-conversion between Na+ and NaCl.

Caused by the exhaustion of the pure water, the flow switch 14b operates to open the valve 2, and thereafter the above mentioned measuring operation is repeated. This enables continuous monitoring. In this case, the quantity of the air to be supplied is measured by the flow meter 11 and is regulated by the valve 9. The time period during which the air is supplied can be regulated by the timer 14. Furthermore, the time period during which the super pure water is supplied can be regulated by a means (not shown) provided in the means 30 for supplying the super pure water.

Besides, it is, of course, possible to control the quantity of air and the time period for bubbling depending on the density of salts in the atmosphere at the place where the measurement is conducted. The sodium ion analyzer has a measuring range from 0.01 ppb to 1.000 ppb, and it may be provided with an alarming function to output an alarm signal when the measured result exceeds the upper limit of the measuring range as a countermeasure against a high density of salts in a seaside region.

According to the present invention, a predetermined quantity of air in the atmosphere is bubbled into a predetermined quantity of super pure water, and the density of Na+ ions in the exhausted super pure water of a predetermined quantity is measured by a sodium ion analyzer. Such construction makes it possible to obtain the absolute value of salts in atmosphere, and further to continuously monitor the same.

What is claimed is:

1. A device for measuring the absolute value of the density of salts in atmosphere, which comprises:
    an airtight water tank containing super pure water of a predetermined quantity;
    a means for bubbling a predetermined quantity of air from the atmosphere for a predetermined time into the super pure water to make the salts in the air dissolve in the water;
    a means for exhausting the super pure water after the bubbling; and
    a sodium ion analyzer for measuring the density of sodium ions in the exhausted super pure water of a predetermined quantity.

* * * * *